United States Patent [19]
Fitting

[11] Patent Number: 5,573,719
[45] Date of Patent: Nov. 12, 1996

[54] PROCESS OF MAKING HIGHLY ABSORBENT NONWOVEN FABRIC

[75] Inventor: Steven W. Fitting, Acworth, Ga.

[73] Assignee: Kimberly-Clark Corporation, Neenah, Wis.

[21] Appl. No.: 346,792

[22] Filed: Nov. 30, 1994

[51] Int. Cl.⁶ .......................... B29C 55/06; B29C 69/00
[52] U.S. Cl. .................... 264/129; 264/156; 264/210.6; 264/288.8; 264/342 RE; 427/172; 427/176
[58] Field of Search .................. 264/129, 154, 264/156, 210.6, 211, 288.8, 342 RE; 427/172, 176, 384

[56] References Cited

U.S. PATENT DOCUMENTS

| | | | |
|---|---|---|---|
| 3,038,215 | 6/1962 | Harwood | 28/106 |
| 3,692,618 | 9/1972 | Dorschner et al. | 428/227 |
| 3,709,764 | 1/1973 | Thomas | 156/177 |
| 3,747,161 | 7/1973 | Kalwaites | 28/105 |
| 3,802,817 | 4/1974 | Matsuki et al. | 425/66 |
| 3,949,128 | 4/1976 | Ostermeier | 428/152 |
| 4,107,364 | 8/1978 | Sisson | 428/196 |
| 4,307,143 | 12/1981 | Meitner | 252/91 |
| 4,340,563 | 7/1982 | Appel et al. | 264/518 |
| 4,436,780 | 3/1984 | Hotchkiss et al. | 428/198 |
| 4,443,513 | 4/1984 | Meitner et al. | 422/195 |
| 4,486,485 | 12/1984 | Sookne | 428/198 |
| 4,578,414 | 3/1986 | Sawyer et al. | 524/310 |
| 4,606,964 | 8/1986 | Wideman | 428/152 |
| 4,657,802 | 4/1987 | Morman | 428/152 |
| 4,720,415 | 1/1988 | Vander Wielen et al. | 428/152 |
| 4,734,311 | 3/1988 | Sokolowski | 428/152 |
| 4,741,941 | 5/1988 | Englebert et al. | 428/71 |
| 4,741,944 | 5/1988 | Jackson et al. | 428/152 |
| 4,781,966 | 11/1988 | Taylor | 428/152 |
| 4,863,779 | 9/1989 | Daponte | 428/152 |
| 4,886,632 | 12/1989 | Van Iten et al. | 264/156 |
| 4,904,521 | 2/1990 | Johnson et al. | 428/284 |
| 4,906,513 | 3/1990 | Kebbell et al. | 428/198 |
| 4,935,287 | 6/1990 | Johnson et al. | 428/198 |
| 4,965,122 | 10/1990 | Morman | 428/225 |
| 4,981,747 | 1/1991 | Morman | 428/198 |
| 5,057,361 | 10/1991 | Sayovitz et al. | 428/290 |
| 5,114,781 | 5/1992 | Morman | 428/198 |
| 5,116,662 | 5/1992 | Morman | 428/198 |
| 5,188,625 | 2/1993 | Van Iten et al. | 604/383 |
| 5,223,319 | 6/1993 | Cotton et al. | 428/131 |

*Primary Examiner*—Leo B. Tentoni
*Attorney, Agent, or Firm*—Michael U. Lee; William D. Herrick

[57] ABSTRACT

The invention provides a process for producing a highly absorbent, high strength wiper, which includes the steps of providing a bonded nonwoven web selected from the group consisting of spunbond fiber webs and staple fiber webs, stretching the nonwoven web by applying a stretching tension in at least one direction, aperturing the nonwoven web while maintaining the stretching tension, and relaxing the apertured web, thereby returning the apertured nonwoven web substantially to its pre-stretched dimensions, wherein the process is conducted at a temperature below the softening point of the nonwoven web. The invention also provides a nonwoven wiper produced in accordance with the production process.

15 Claims, 3 Drawing Sheets

PROCESS OF MAKING HIGHLY ABSORBENT NONWOVEN FABRIC

BACKGROUND OF THE INVENTION

The present invention is related to a highly absorbent nonwoven fabric and a process for producing the same. More particularly, the invention is related to a nonwoven fabric that has a high capacity for absorbing polar and nonpolar liquids.

Domestic and industrial wipers are used to quickly pick up both polar liquids, e.g., water and alcohols, and nonpolar liquids, e.g., oil, and these wipers should have a sufficient capacity to hold the absorbed liquid within the wiper structure until it is desired to remove the liquid by pressure such as wringing. Additional necessary properties for wipers are high physical strength and abrasion resistance in that wipers must be able to withstand the tearing, stretching and abrading forces applied during use and should be relatively lint free.

Nonwoven fabrics, especially meltblown nonwoven webs, have been widely used as wipers, especially as disposable wipers. Meltblown nonwoven webs, containing microfibers, have an interfiber capillary structure that is highly suitable for absorbing and retaining liquid. However, meltblown nonwoven webs may not have sufficiently high physical properties, e.g., tear strength and abrasion resistance, that are needed for heavy duty wiper applications and tend to produce lint. Consequently, meltblown nonwoven webs are typically laminated to a support layer, e.g., a spunbond nonwoven fabric, for heavy duty uses and may not make appropriate wipers for uses on abrasive or rough surfaces.

Spunbond and staple fiber nonwoven webs, which contain thicker and stronger fibers than the microfibers of meltblown nonwoven webs and typically are point bonded with heat and pressure, provide desirable strength properties, including tear strength and abrasion resistance. However, spunbond and staple fiber nonwoven webs, which contain relatively thick fibers do not tend to provide fine interfiber capillary structures and thus are less suitable for handling liquid. Furthermore, spunbond and staple fiber nonwoven webs contain bond points that do not have any interfiber structure altogether and form barriers to the flow or transfer of liquid within the nonwoven webs. Spunbond and staple fiber nonwoven webs have not been used widely in wiper applications.

There remains a need for a high strength nonwoven web that exhibits improved absorbent properties along with desirable strength properties.

SUMMARY OF THE INVENTION

The invention provides a process for producing a highly absorbent and high strength wiper, which comprises the steps of providing a bonded nonwoven web selected from the group consisting of spunbond fiber webs and staple fiber webs, stretching the nonwoven web by applying a stretching tension in at least one direction, aperturing the nonwoven web while maintaining the stretching tension, and relaxing the apertured web, thereby returning the apertured nonwoven web substantially to its pre-stretched dimensions, wherein the process is conducted at a temperature below the softening point of the nonwoven web. The invention also provides a nonwoven wiper produced in accordance with the production process.

The present nonwoven wiper containing spunbond or staple fibers provides high absorbency as well as high tear strength and abrasion resistance.

DETAILED DESCRIPTION OF THE INVENTION

The present invention provides a process for producing nonwoven wiper webs that are highly suitable for various wiper applications. The present nonwoven wiper webs exhibit high absorbent capacities for both polar and nonpolar liquids as well as provide high physical strength and integrity. The nonwoven wipers also provide pleasing textural properties, including a soft, cloth-like texture.

The nonwoven wipers of the invention are produced from bonded spunbond nonwoven webs and staple fiber nonwoven webs. According to the present invention, the nonwoven wipers are produced by a process which has the steps of providing a bonded nonwoven web, stretching the nonwoven web, aperturing the web while maintaining the stretching tension, and relaxing the apertured web, thereby returning the apertured nonwoven web approximately to its prestretched dimensions. The stretching and aperturing steps of the absorbent nonwoven wiper production process are conducted at a temperature below the softening point of the polymer of the nonwoven webs, i.e., the nonwoven webs are not heated to a temperature that is equal to or higher than the softening temperature of the polymer constituting the nonwoven web. More desirably, the nonwoven webs are processed at a temperature below the heat deflection temperature of the polymer of the nonwoven web that is determined in accordance with ASTM D-648 at 66 psi. Most desirably, the stretching and aperturing steps are conducted at ambient room temperature.

Figure 1:
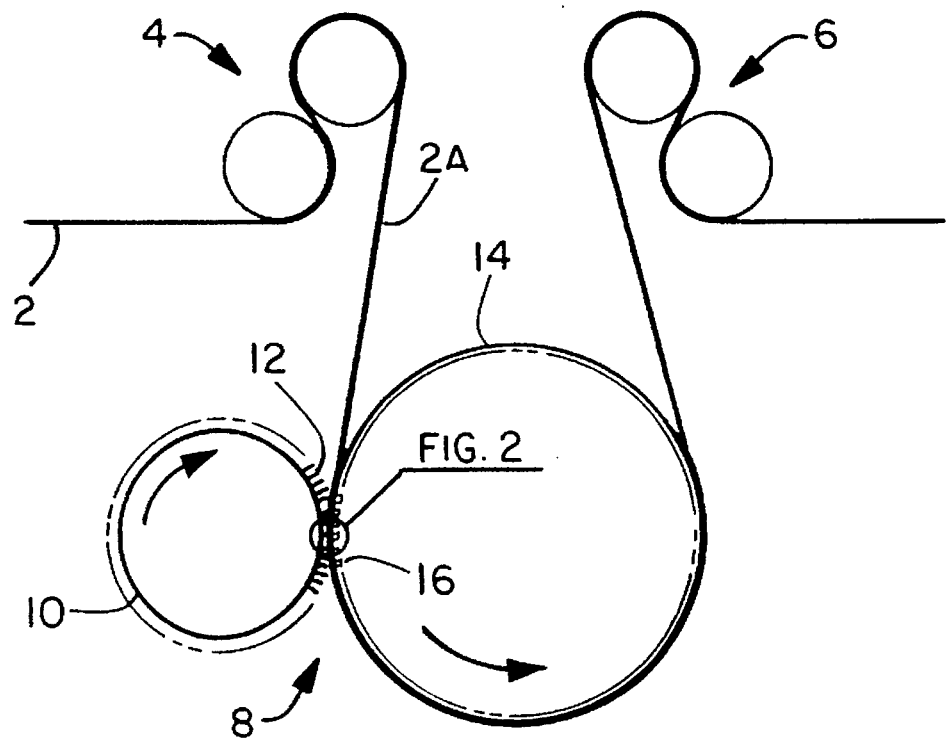
FIG. 1 illustrates an exemplary stretching and aperturing process.

In accordance with the present invention, the stretching step can be effected with any known fabric or film stretching process that applies stretching tension in the machine, cross-machine or both machine and cross machine directions. An illustrative example of suitable stretching processes is shown in FIG. 1. A bonded nonwoven web 2 is passed through two sets of S-roll arrangements, a first S-roll arrangement 4 and a second S-roll arrangement 6. Each S-roll arrangement contains at least two closely positioned, counter rotating rolls that advance the nonwoven web without significant slippage. The peripheral linear speed of the second S-roll arrangement 6 is controlled to be faster than the linear speed of the first S-roll arrangement 4 so that the nonwoven web is stretched in the machine direction. Another example of suitable stretching processes is a tenter frame process which utilizes gripping means, e.g., clips, to hold the edges of the nonwoven and apply the stretching force, typically in the cross-machine direction. Although the desirable degree of stretch may vary widely, in general, a higher level of stretch results in an absorbent nonwoven web having a higher absorbent capacity. Desirably, the nonwoven web is not stretched beyond its elastic limit, i.e., the point where a permanent deformation occurs. As a highly suitable embodiment of the present invention, the nonwoven web desirably is stretched up to about 50%, more desirably in the range of from about 5% to about 40%, most desirably in the range of from about 10% to about 30%. The degree of stretch, as used herein, is calculated by dividing the difference in the stretched dimension, e.g., width, between the initial nonwoven web and the stretched nonwoven web by the initial dimension of the nonwoven web.

The aperturing step of the present invention can be conducted in an aperturing apparatus that can be illustrated as having a pin member containing a series of pins and an orifice member containing a series of indentations or orifices that correspondingly receive the pins. The aperturing process of the present invention can be characterized as providing regions adjacent the apertures of substantially unconsolidated fibers, i.e., the fibers adjacent the apertures generally have some degree of freedom of movement and are not fixed in position with respect to the other fibers of the web. Desirably, the apparatus is a rotary aperturing system with the capacity of accommodating a variety of shapes of pins. Suitable pins and thus the corresponding orifices may have a variety of cross-sectional base shapes including circular, oval, rectangular and triangular shapes. Desirably, suitable pins have a circular cross-sectional shape. Hereinafter, the present invention is described with cylindrical pins having a circular cross-sectional shape for the purpose of illustration. According to the present invention, the pins desirably have a diameter between about 0.03 and about 0.25 of an inch. In addition, the pins may have a chamfered end to facilitate the aperturing process. Depending on the uses and the thickness of the nonwoven webs, the depth of penetration of the pins through the web may vary, e.g., complete or incomplete penetration. In general, a nonwoven web containing completely penetrated apertures provides a higher absorbent capacity. According to the present invention, the number of pins aperturing a unit area of the nonwoven web may vary widely. The pin density suitable for the present invention is between about 6 pins and about 400 pins, more desirably between about 50 pins and about 200 pins, most desirably between about 100 pins and about 160 pins, per square inch.

Returning to FIG. 1, there is illustrated an exemplary aperturing process suitable for the present invention. An aperturing nip roller arrangement 8 is placed between the aforementioned two S-roll arrangements, 4 and 6, applying apertures on the tensioned or stretched nonwoven web 2A. The nip roller arrangement 8 contains a pin roller 10 having a plurality of unheated pins 12 and an orifice roller 14 having a plurality of counterpart unheated orifices 16. Each orifice 16 has a diameter that is larger than the diameter of the counterpart pin 12, thereby the pins and the orifices can be inter-engaged without clipping or punching pieces of the nonwoven web at the entrance edge of the orifices. Desirably, the diameter of each orifice is at least about 0.01 inch larger than that of the counterpart pin.

A particularly suitable nip roller arrangement for the present invention is disclosed in U.S. Pat. No. 4,886,632 to Van Iten et al., which is herein incorporated by reference. However, unlike the nip roller arrangement of U.S. Pat. No. 4,886,632, the nip roller arrangement of the present invention is not operated at an elevated temperature so as to avoid melt fusion of the fibers at the edge of the apertures. Melt-fusing the constituent fibers of the nonwoven web during the aperturing step is not desirable for purposes of the present invention in that the melt-fused regions decrease the absorbent capacity of the nonwoven web as well as interrupt the interfiber capillary structure of the web. The interfiber capillary structure is important for the efficient use of wipers since it promotes distribution of the absorbed liquid toward unused or unwetted portions of the web, thereby promoting an efficient use of the wiper.

Figure 2:
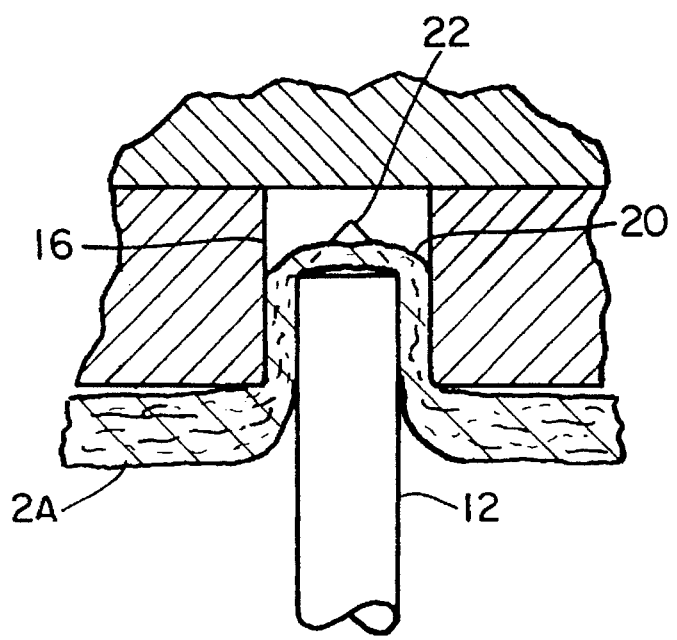
FIG. 2 illustrates an exemplary aperturing process.

In operating the nip roller arrangement 8, the rollers 10 and 14 synchronously rotate while the stretched web 2A is fed through the nip formed by the rollers. As the rollers rotate, the pins 12 of the roller 10 push the fibers of the nonwoven web 2A into the counterpart orifices 16. The aperturing step is further illustrated in FIG. 2. When the nonwoven web 2A is pushed into the orifice 16 by the pin 12, the nonwoven web forms a raised region 20 and a penetrated aperture 22. The degree of penetration can be controlled by adjusting the proximity of the nip rollers 10 and 14 and/or the length of the pins 12.

Figure 3:
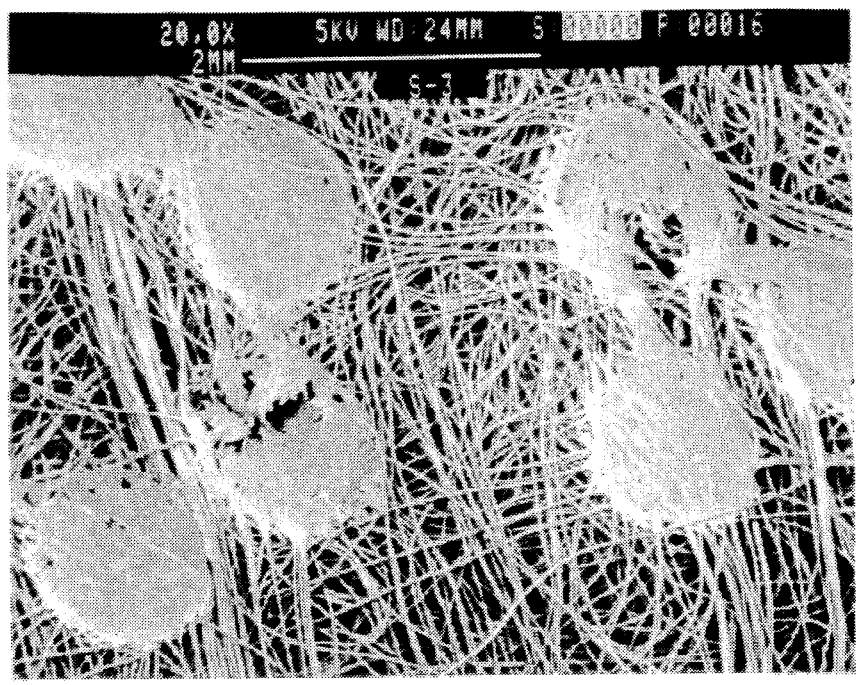
FIGS. 3–4 are microphotographs of the present wiper.
Figure 4:
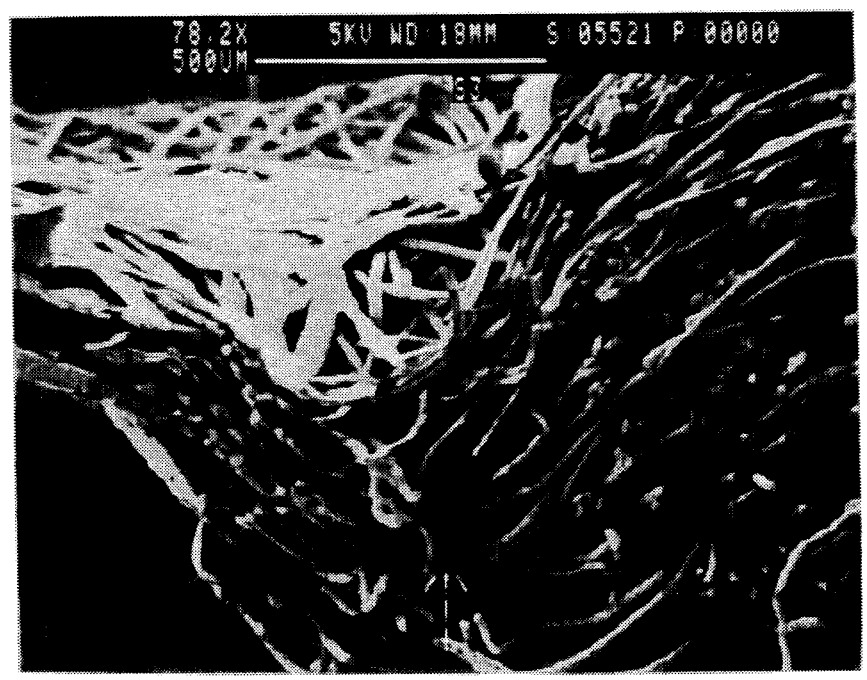
Figure 5:
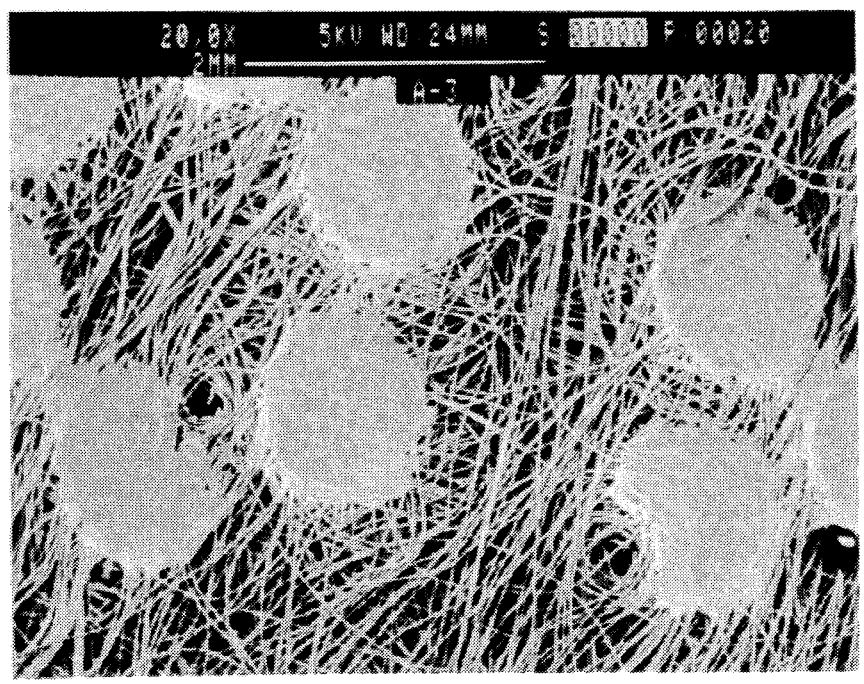
FIGS. 5–6 are microphotographs of a wiper that was apertured without stretching tension.
Figure 6:

After effecting the apertures, the stretching tension applied on the nonwoven web is released to return the nonwoven web substantially to its pre-tensioned dimensions. Desirably, the stretched dimension of the apertured nonwoven web returns to within about 125%, more desirably within about 110%, of the pre-tensioned length when the stretching tension is released. Most desirably, the apertured nonwoven web returns to its original dimensions. Compared to apertured nonwoven webs produced without the stretching tension, the apertures of the present nonwoven wiper web are not as conspicuously and readily ascertainable. FIGS. 3–6 further illustrate the wiper of the present invention. FIGS. 3 and 4 are a top view and a cross-sectional view, respectively, of a spunbond nonwoven web that was apertured while applying a 20% stretching tension and is highly suitable for the present wiper, and FIGS. 5 and 6 are corresponding views of a similar spunbond nonwoven web that was apertured without the stretching tension. Even at this magnification level, the apertures in FIG. 3 are not as clearly defined as the apertures in FIG. 5. FIG. 4 shows that the fibers adjacent the apertures are generally unconsolidated and bulked up. In addition, the apertures disrupt some portions of the bond points of the nonwoven web, especially the secondary bond points, thereby further increasing the bulk of the nonwoven web. The term secondary bond points indicates regions of fused fibers that are formed between adjacent main bond points, which further stiffen and densify the nonwoven web. FIGS. 5 and 6 clearly demonstrate that when a bonded nonwoven web is apertured without the stretching tension, the fibers around the apertures merely get rearranged to form voids and do not tend to bulk up the nonwoven web. It is to be noted that the aperturing process of the present invention, which unconsolidates portions of the nonwoven web, not only improves the absorbent capacity but also improves textural properties of the nonwoven web.

Nonwoven webs suitable for the present invention include bonded spunbond nonwoven webs and staple fiber nonwoven webs, and the fibers forming the suitable nonwoven webs can be monocomponent fibers, multicomponent conjugate fibers or mixtures thereof. Suitable nonwoven webs may additionally contain natural fibers, e.g., wood pulp, cotton fibers and the like, as well as natural and synthetic superabsorbent particles, e.g. polyacrylamides, polyarylic acids and metal salts of polyacrylic acid. Suitable fibers for the wiper webs have an average diameter between about 8 μm and about 55 μm or higher, and suitable nonwoven webs desirably have a basis weight of at least about 1 ounce per square yard (osy), more desirably between about 1.5 osy and about 3 osy. The term "spunbond fiber web" refers to a nonwoven fiber web of small diameter filaments that are formed by extruding a molten thermoplastic polymer as filaments from a plurality of capillaries of a spinneret. The extruded filaments are partially cooled and then rapidly drawn by an eductive or other well-known drawing mechanism to effect the molecular orientation of the filament polymer and thus to improve the physical strength of the filaments. The drawn filaments are deposited or laid onto a forming surface in a random, isotropic manner to form a loosely entangled nonwoven fiber web, and then the laid web is subjected to a bonding process to impart physical integrity and dimensional stability. Bonding processes suitable for spunbond fiber webs are well known in the art, which include calender bonding and ultrasonic bonding processes, and suitable bonding processes provide discrete bonded regions substantially uniformly throughout the nonwoven web. The production of spunbond webs is disclosed, for example, in U.S. Pat. Nos. 4,340,563 to Appel et al., 3,802,817 to Matsuki et al. and 3,692,618 to Dorschner et al. Typically, spunbond fibers have an average diameter between about 8 μm and about 55 μm or higher, although finer spunbond fibers can be produced. The term "staple fiber nonwoven web" refers to a nonwoven web that is formed from staple fibers. Staple fibers are produced with a conventional staple fiber spinning and drawing processes and then cut to a staple length, from about 1 inch to about 8 inches. Using carding, air-laying or wet-laying techniques, the staple fibers are deposited onto a forming surface and then bonded to form a nonwoven web. The term "monocomponent fibers" indicates fibers and filaments fabricated from a relatively homogeneous polymer composition of one polymer or a blend of two or more polymers. The term "multicomponent conjugate fibers" refers to fibers and filaments fabricated from at least two polymeric components which are arranged to occupy distinct sections in substantially the entire length of the fibers. Conjugate fibers are formed by simultaneously extruding at least two molten polymeric compositions as a plurality of unitary multicomponent fibers or filaments. Of these suitable nonwoven webs, particularly suitable are spunbond nonwoven webs since spunbond nonwoven webs containing continuous fibers are less likely to produce lint and since spunbond nonwoven web production processes involve less manufacturing steps, e.g., no staple forming and carding steps, than staple fiber web production processes.

Suitable fibers for the present nonwoven web can be produced from a wide variety of thermoplastic polymers that are known to form fibers. Suitable polymers for the present invention include, but are not limited to, polyolefins, polyamides, polyesters, and blends and copolymers thereof, as well as copolymers containing acrylic monomers. Suitable polyolefins include polyethylene, e.g., linear low density polyethylene, high density polyethylene, low density polyethylene and medium density polyethylene; polypropylene, e.g., isotactic polypropylene, syndiotactic polypropylene, blends thereof and blends of isotactic polypropylene and atactic polypropylene; polybutylene, e.g., poly(1-butene) and poly(2-butene); and polypentene, e.g., poly-4-methyl-pentene-1 and poly(2-pentene); as well as blends and copolymers thereof. Suitable polyamides include nylon 6, nylon 6/6, nylon 10, nylon 4/6, nylon 10/10, nylon 12, nylon 6/12, nylon 12/12, and hydrophilic polyamide copolymers such as copolymers of caprolactam and an alkylene oxide, e.g., ethylene oxide, and copolymers of hexamethylene adipamide and an alkylene oxide, as well as blends and copolymers thereof. Suitable polyesters include polyethylene terephthalate, polybutylene terephthalate, polycyclohexylenedimethylene terephthalate, and blends and copolymers thereof. Acrylic copolymers suitable for the present invention include ethylene acrylic acid, ethylene methacrylic acid, ethylene methylacrylate, ethylene ethylacrylate, ethylene butylacrylate and blends thereof. Of the above illustrated suitable polymers, particularly suitable polymers for the present invention are polyolefins, and more particularly suitable are polypropylene and polyethylene. Suitable fiber forming polymer compositions may additionally have thermoplastic elastomers blended therein as well as contain pigments, fragrances, abrasive particles, filler and the like.

As is known in the art, most of conventional thermoplastic polymers are inherently hydrophobic and non-polar. Consequently, nonwoven webs produced from these polymers are highly suitable for handling nonpolar liquids, e.g., oils and liquid petrochemicals. However, when a wiper suitable for both polar and nonpolar liquids is desired, the nonwoven web or the fibers forming the nonwoven web need to be modified to additionally provide necessary affinity for polar and/or aqueous liquids. There are two suitable approaches in modifying the nonwoven web or the fibers. One is post-fabrication modification and the other is pre-fabrication modification. A typical post-fabrication modification topically applies, e.g., spray, dip, coat or print, a modifying agent onto fully formed fibers or nonwoven webs, which is then dried or cured to affix the agent. An exemplary topical modification process is disclosed in U.S. Pat. No. 5,057,361 to Sayovitz et al. A typical pre-fabrication modification blends in a minor amount of a modifying agent in the fiber-forming polymer composition before the composition is spun into fibers or filaments. The modifying agent can be dry blended into the polymer composition before the composition is extruded or injected directly into the extruding apparatus while the polymer composition is being extruded. An exemplary composition modification process is disclosed in U.S. Pat. No. 4,578,414 to Sawyer et al. Both of the patents are herein incorporated by reference. Suitable modifying agents for the present invention include various surfactants that are suitably compatible with the above-illustrated fiber-forming polymers. Suitable surfactants include ionic, nonionic and zwitterionic surfactants. Illustrative of these are dioctyl sodium sulfosuccinate; octylphenoxypolyethyoxy ethanol; alkenyl succinamide salt; polyoxyalkylene alkyl phenols, e.g., polyoxyethylene octphenol ether and polyoxyethylene nonylphenol ether; polyoxyalkylene modified fatty acids, e.g., polyoxyethylene oleate, polyoxyethylene stearate and polyethylene glycol monolaurate; polyoxyalkylene modified siloxanes and silanes, e.g., polyoxyethylene dimethyl siloxane; polyoxyalkylene modified fluoroaliphatic compounds, e.g., polyoxyethylene modified fluoroaliphatic compounds; and mixtures thereof. Commercially available surfactants suitable for the present invention include various poly(ethylene oxide) based surfactants available under the tradename Triton, e.g., grade X-102, from Union Carbide Crop; various polyethylene glycol based surfactants available under the tradename Emerest, e.g., grades 2620 and 2650, from Emery Industries; various polyalkylene oxide modified polydimethylsiloxane based surfactants available under the tradename Silwet, e.g., grade Y12488, from OSI Specialty Chemicals; alkenyl succinamide surfactants available under the tradename Lubrizol, e.g, grade OS85870, from Lubrizol Crop.; and polyoxyalkylene modified fluoroaliphatic surfactants available from Minnesota Mining and Manufacturing Co. In general, the surfactant may be added, topically or internally, in the range of from about 0.1% to about 5%, desirably from about 0.5% to about 4%, more desirably from about 1% to about 3%, by weight based on the weight of the fiber or the nonwoven web.

The nonwoven wiper of the present invention is highly suitable for domestic and industrial wiper applications handling a wide variety of polar and nonpolar liquids. The wiper is a highly absorbent and low linting wiper that provides excellent tear resistance, tensile strength and abrasion resistance while exhibiting highly pleasing, soft textural properties.

The present invention is further described with the following examples, which are provided for illustration purposes, and the invention is not limited thereto.

EXAMPLES

Testing Procedure

Oil and Water Capacities

The capacity refers to the amount of oil or water that a sample of a nonwoven web will hold. A sample 7 inches by 11 inches of a nonwoven web is cut and weighed (initial weight). After soaking for 1 minute in Blandol white mineral oil having a specific gravity in the range of 0.845 to 0.860 or tap water at 60° C., the sample is removed and allowed to drip for 1 minute, and then reweighed (soaked weight). The capacity, in percent, is calculated as follows: (soaked weight/initial weight)×100.

Grab Tensile Strength and Elongation

The grab test for tensile strength and elongation measures the breaking load and percent elongation just before rupture of a nonwoven web at a constant rate of extension in a single direction. The test was conducted in accordance with Method 5100—Federal Test Methods Standard No. 191A (1978).

Drape Stiffness

This test determines the bending length of a nonwoven web using the principle of cantilever bending of the web under its own weight. The test was conducted in accordance with ASTM D-1388-64, except the specimen size was 1 inch by 8 inches rather than 1 inch by 6 inches.

EXAMPLES 1–5 (Ex1–Ex5)

Point bonded spunbond nonwoven webs having an approximately 2 ounce per square yard basis weight were produced in accordance with the process described in above-mentioned U.S. Pat. No. 3,802,817 to Matsuki et al. from polypropylene pellets. Polypropylene, PD3443, which is available from Exxon, was blended with 2 wt % of a $TiO_2$ concentrate containing 50 wt % of $TiO_2$ and 50 wt % of polypropylene, and the mixture was melt-extruded in a single screw extruder and then spun into spunbond filaments. The spun filaments were deposited onto a foraminous forming surface and then point bonded in a calender bonder. The bonded nonwoven webs contained 28% of bonded regions and are available under the tradename Accord from Kimberly-Clark Corp. Subsequently, the nonwoven webs were topically treated to have 0.5 wt %, based on the weight of the nonwoven web, of a dioctyl sodium sulfosuccinate surfactant, Gemtex™ SM-33, available from Finetex, N.J.

The treated nonwoven webs were apertured under a stretching tension and a pin penetration depth, as indicated in Table 1, using the apparatus described in U.S. Pat. No. 4,886,632 to Van Iten et al. The tensioned nonwoven webs were apertured at ambient room temperature with an unheated nip roller arrangement that applied about 120 apertures per square inch. The orifices had an inside diameter of 0.096 inches and an inside depth of 0.23 inches. The pins were made of hard steel and had a shaft diameter of 0.072 inches, a length of 0.63 inches and a penetrating point chamfer angle of 60°. The apertures in the nonwoven webs were not highly noticeable. The wipers were tested for various properties and the results are shown in Table 1.

COMPARTIVE EXAMPLE 1 (C1)

A pre-apertured sample of the bonded nonwoven web of Example 1 was tested for its properties, and the results are shown in Table 1.

COMPARTIVE EXAMPLE 2–4 (C2–C4)

Apertured nonwoven webs were produced in accordance with Examples 1–3, except the nonwoven webs were not tensioned while applying the apertures.

COMPARATIVE EXAMPLE 5 (C5)

A bonded nonwoven web was produced in accordance with Example 1, and then the web was subjected to a 20% stretching force and then relaxed. The relaxed nonwoven web was then apertured in the relaxed condition. This comparative example was prepared to demonstrate the importance of the simultaneous application of the stretching and aperturing procedures.

COMPARATIVE EXAMPLE 6 (C6)

Comparative example 5 was repeated, except the stretched nonwoven web was heat set at 170° F., to thermally relax the tension applied on the web. The resulting nonwoven web retained the stretched dimensions. The relaxed web was then cooled and apertured. This comparative example was also prepared to demonstrate the importance of the simultaneous application of the stretching and aperturing procedures.

TABLE 1

| Example | Basis Weight (osy) | Stretching Ratio (%) | Pin Depth (inch) | Oil Capacity (%) | Water Capacity (%) | CD Grab Tensile (kg) | CD Grab Elongation (%) | Drape Stiffness MD (cm) | CD |
|---|---|---|---|---|---|---|---|---|---|
| Ex1 | 2.4 | 9 | 0.116 | 400 | 385 | 13 | 40 | 4.7 | 3.2 |
| Ex2 | 2.0 | 9 | 0.097 | 371 | 368 | — | — | — | — |
| Ex3 | 2.0 | 18 | 0.097 | 409 | 455 | 11 | 39 | 3.5 | 2.9 |
| Ex4 | 2.0 | 22 | 0.080 | 445 | 498 | — | — | — | — |
| Ex5 | 2.0 | 30 | 0.080 | 449 | 530 | — | — | — | — |
| C1 | 1.9 | 0 | N/A | 284 | 267 | 13 | 33 | 4.1 | 3.3 |
| C2 | 2.1 | 0 | 0.116 | 316 | 331 | — | — | — | — |
| C3 | 2.0 | 0 | 0.097 | 304 | 337 | 13 | 38 | 3.6 | 3.0 |
| C4 | 2.0 | 0 | 0.080 | 288 | 322 | — | — | — | — |

TABLE 1-continued

| Example | Basis Weight (osy) | Stretching Ratio (%) | Pin Depth (inch) | Oil Capacity (%) | Water Capacity (%) | CD Grab Tensile (kg) | CD Grab Elongation (%) | Drape Stiffness MD (cm) | CD |
|---|---|---|---|---|---|---|---|---|---|
| C5 | 2.0 | 20 | 0.091 | 310 | 334 | 12 | 56 | — | — |
| C6 | 2.0 | 20 | 0.091 | 311 | 362 | 14 | 44 | — | — |

Note:
MD = machine direction
CD = cross-machine direction

The results in Table 1 show that the absorbent capacities of the present wipers for both oil and water are significantly higher than nonapertured web and, more importantly, are unexpectedly much higher than apertured webs that were produced without the stretching tension. The results also demonstrate that the stretching ratio and the pin penetration depth advantageously improve the absorbency of the wiper web, and that the aperturing process does not significantly diminish or change the physical properties, e.g., tensile and drape stiffness, of the wiper nonwoven web. Comparative Examples 5 and 6 demonstrate that the separately applied stretching tension does not appear to contribute to the improvement of the absorbency of the nonwoven web, and thus the stretching and the aperturing steps must be applied simultaneously in order to take full advantage of the present invention.

The present invention provides a highly absorbent nonwoven wiper that is suitable for various domestic and industrial wiper applications. The nonwoven wiper exhibits high absorbency as well as high physical strength properties and is virtually lint free.

What is claimed is:

1. A process for producing a highly absorbent, high strength wiper, which comprises the steps of:
   a) providing a bonded nonwoven web selected from the group consisting of spunbond fiber webs and staple fiber webs,
   b) stretching said nonwoven web by applying a stretching tension in at least one direction,
   c) aperturing said nonwoven web while maintaining said stretching tension, and
   d) relaxing the apertured web, thereby returning the apertured nonwoven web substantially to its pre-stretched dimensions and forming said wiper,
   wherein said process is conducted at a temperature below the softening point of said nonwoven web.

2. The wiper production process of claim 1 wherein the aperturing step imparts between about 6 and about 400 apertures per square inch.

3. The wiper production process of claim 1 wherein the aperturing step imparts between about 100 and about 160 apertures per square inch.

4. The wiper production process of claim 1 wherein the stretching step stretches said bonded nonwoven web to a point below the elastic limit of said web.

5. The wiper production process of claim 4 wherein said bonded nonwoven web is stretched up to about 50%.

6. The wiper production process of claim 4 wherein said bonded nonwoven web is stretched between about 5% and about 40%.

7. The wiper production process of claim 1 wherein said nonwoven web is a spunbond fiber web.

8. The wiper production process of claim 1 wherein said nonwoven web has a basis weight of at least about 1 ounce per square yard.

9. The wiper production process of claim 1 wherein said nonwoven web comprises a fiber-forming polymer selected from the group consisting of polyolefins, polyamides, polyesters, acrylic copolymers, and blends and copolymers thereof.

10. The wiper production process of claim 1 wherein said nonwoven web comprises a fiber-forming polymer selected from the group consisting of polyethylene, polypropylene, and blends and copolymers thereof.

11. The wiper production process of claim 9 wherein said nonwoven web further comprises a surfactant.

12. The wiper production process of claim 11 wherein said surfactant is topically applied.

13. The wiper production process of claim 11 wherein said surfactant is blended with said fiber-forming polymer.

14. The wiper production process of claim 11 wherein said surfactant is selected from the group consisting of polyoxyalkylene alkyl phenols, polyoxyalkylene modified fatty acids, polyoxyalkylene modified siloxanes, polyoxyalkylene modified fluoroaliphatic compounds, and mixtures thereof.

15. The wiper production process of claim 1 wherein the fibers of said bonded nonwoven web have an average diameter between about 8 μm and about 55 μm.

* * * * *